United States Patent [19]
Stokes et al.

[11] Patent Number: 5,376,267
[45] Date of Patent: Dec. 27, 1994

[54] CYTOCENTRIFUGE ROTOR FOR CYTOCENTRIFUGATION DEVICES

[75] Inventors: Barry O. Stokes; Carmelo G. Quirante, both of Logan, Utah

[73] Assignee: Wescor, Inc., Logan, Utah

[21] Appl. No.: 105,893

[22] Filed: Aug. 11, 1993

Related U.S. Application Data

[62] Division of Ser. No. 788,310, Nov. 5, 1991, Pat. No. 5,252,228.

[51] Int. Cl.$^5$ .................................................. B04B 5/02
[52] U.S. Cl. ...................................... 210/361; 422/72; 422/101; 494/16; 494/36
[58] Field of Search ................... 210/361, 362; 118/52; 494/10, 16, 36, 44, 45; 422/72, 101, 102

[56] References Cited

U.S. PATENT DOCUMENTS

| | | | |
|---|---|---|---|
| 3,834,613 | 9/1974 | Hankey | 118/52 |
| 4,306,514 | 12/1981 | Bouclier | 118/52 |
| 4,391,710 | 7/1983 | Gordon | 210/361 |
| 4,423,699 | 1/1984 | Boeckel et al. | 118/52 |
| 4,428,323 | 1/1984 | Wells | 118/52 |
| 4,574,729 | 3/1986 | Wells | 118/52 |
| 4,678,579 | 7/1987 | Griffin | 210/477 |

OTHER PUBLICATIONS

A Slide Centrifuge Journal of Laboratory Clinical Medicine 1966, vol. 68, 494–501.
Ames Makes Cytocentrifugation Trade Literature 1987.

*Primary Examiner*—Matthew O. Savage
*Attorney, Agent, or Firm*—Mallinckrodt & Mallinckrodt

[57] ABSTRACT

A cytocentrifugation device, rotor, and apparatus are improved by providing the device with a plurality of liquid-receiving chambers arranged serially along and opening into an elongate conduit leading to and terminating within a filter-pad-holder so that a filter-pad-prewetting liquid can be passed along such conduit and into a liquid-flow opening of a filter pad held by such holder in advance of passage along said conduit and through such liquid-flow opening in the filter pad of a cell-carrying liquid sample during a centrifugation run of the apparatus. Retention of prewetting liquid in the filter pad around the sample liquid flow helps to prevent loss of cells to the filter pad. Various other structural modifications of the cytocentrifugation device and filter pads used therewith also help to prevent loss of cells to the filter pad.

10 Claims, 3 Drawing Sheets

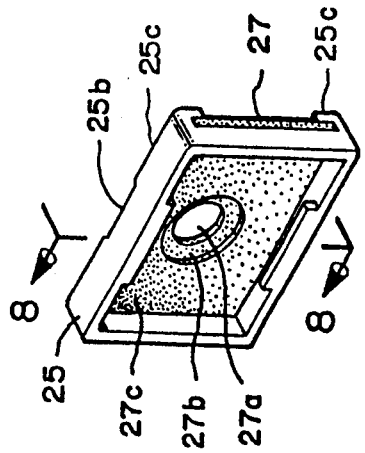
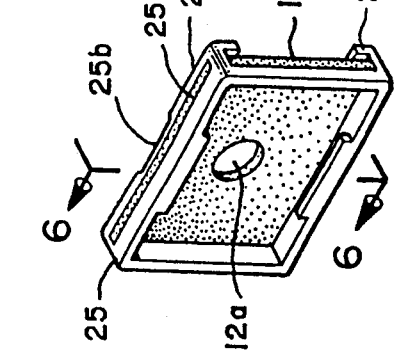
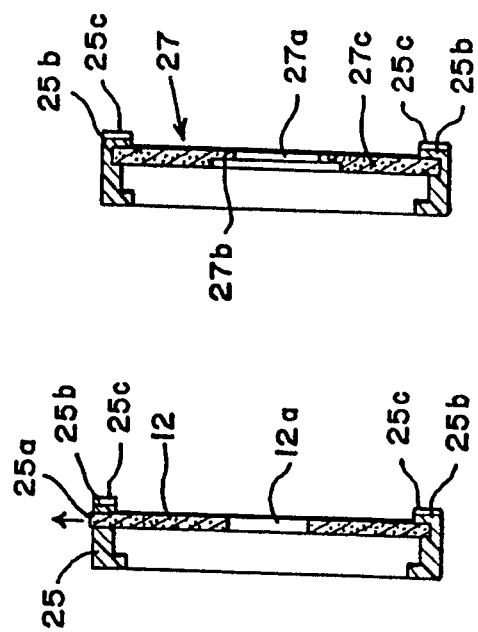
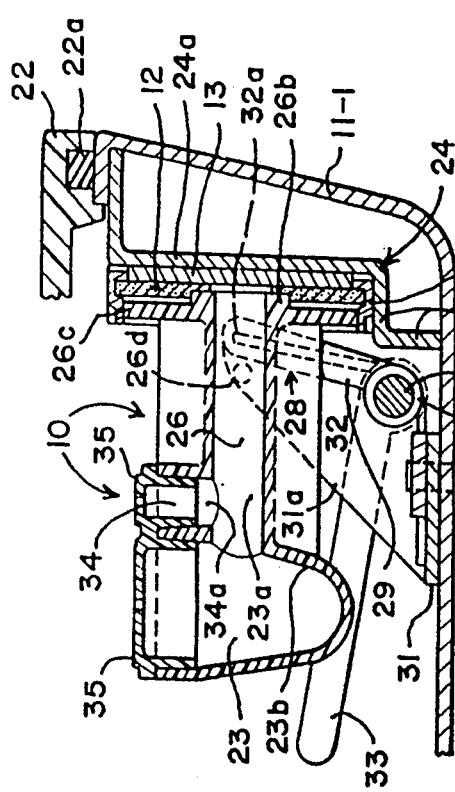
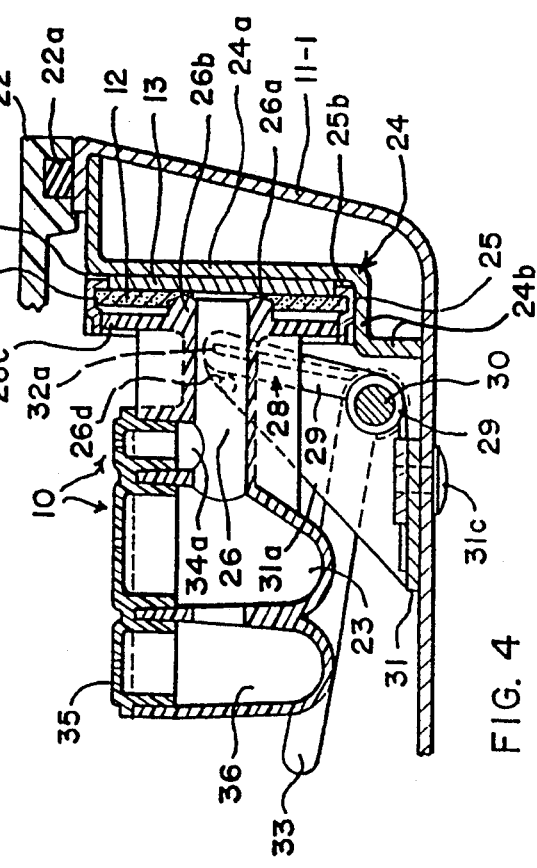

CYTOCENTRIFUGE ROTOR FOR CYTOCENTRIFUGATION DEVICES

This is a division of application Ser. No. 07/788,310, filed Nov. 5, 1991 now U.S. Pat. No. 5,252,228.

BACKGROUND OF THE INVENTION

1. Field

The invention is in the general field of medical laboratory equipment and is particularly concerned with cytocentrifuges, i.e. apparatus for centrifugally depositing, on microscope slides, cells from a liquid suspension of same and with methods of using such apparatus.

2. State of the Art

Apparatus of the type concerned have been developed heretofore and are widely used. Perhaps the best known cytocentrifuge is the "Cytospin" produced by or under the auspices of Shandon Southern Products Limited, Rancorn, England, as shown by Gordon U.S. Pat. Nos. 4,391,710 of Jul. 5, 1983 and by Griffin 4,678,579 of Jul. 7, 1987. There, as in other apparatus of the type concerned, a liquid suspension of cells to be deposited on a microscope slide is placed in a sample chamber of a cytocentrifuge device, normally one adapted for installation in a centrifuge that is adapted to receive a plurality of such devices, each equipped with a sample chamber, a filter pad holder, and a slide holder, so multiple microscope slides can be prepared at the same time, such liquid suspension of cells being passed by centrifugal force from sample chamber to slide surface through an opening in a filter pad that is clamped against the receiving surface of the slide for both sealing so far as possible against lateral passage and consequent loss of the cell-carrying liquid with its cells and for absorbing the liquid component of such cell-carrying liquid upon deposit of the cells on the slide.

Alan J. Gordon, inventor in the aforesaid U.S. Pat. No. 4,341,710, improved pre-existing machines for Shandon in various respects, primarily by incorporating slide and filter card clamping means as part of a sample chamber unit that is removable unitarily (with clamping means) from a centrifuge rotor of the cytocentrifuge.

Prewetting of the liquid-absorbent filter pad has been resorted to in some instances prior to centrifugation to minimize attraction for the cell-carrying liquid sample as it passes toward the microscope slide, with consequent diversion into the filter pad with loss of cells before they have a chance to adhere to the slide.

Also, utilizing a sample chamber having depth that normally dams against liquid outflow except under centrifuging action has been tried in the past for both centrifugal chemical analyzers and cytocentrifuges, see particularly the N. G. Anderson article entitled "The Development of Fast Analyzers", Z. Anal. Chem. 257–271 (1972), and Wells U.S. Pat. No. 4,428,323 of Jan. 31, 1984, respectively.

Prior to the development of cytocentrifuges utilizing centrifugal force to propel a sample of a cell-carrying liquid toward and onto a microscope slide, application of cells onto microscope slides was accomplished by sedimentation techniques utilizing gravity to flow samples of a cell-carrying liquid onto the slides, see the article in *ActaCytologica* 8, 234–241 (1964) by G. Th. A. M. Bots et al.

Present day cytocentrifuges do significantly better than the sedimentation technique. This is accomplished by the use of high centrifugal speeds, wherein sedimentation velocity of cells suspended in the cell-carrying liquid onto the slide is considerably greater than the hydraulic force exerted laterally of the slide face on which the cells are to be deposited.

In practice, present systems employ a trade-off between filter pad thickness governing liquid-holding capacity and a conveniently handled clamping force holding the filter pad against the slide during centrifugation. This places practical constraints on the range of performance characteristics of current systems. For example, if a very slow liquid flow rate into the filter pad is desired, with a convenient clamping spring force, a very thin filter pad must be employed. Under these conditions, the quantity of the sample will be limited to the volume of liquid that such filter pad will hold. If a larger quantity of the sample liquid is involved, a relatively thick filter pad should be employed to receive and retain the greater quantity of liquid component of the liquid sample, but then the flow rate can be too fast to allow good cell recovery.

Loss of cells is also suffered in the transition from the stationary state of the loaded sample chamber to the ultimate steady state speed of operation. Such loss is most severe when the sample liquid comes into contact with the filter pad prior to initiation of centrifugation. Lateral flow into the filter without centrifugation takes place as permitted by the clamping force, filter characteristics, and system geometry. With no centrifugal force to sediment the cells against the slide, the cells tend to flow into the filter with the liquid. If a large fraction of the sample flows into the filter under these conditions, a correspondingly large fraction of the cells can be lost. It has therefore been recognized that some means must be provided to prevent premature contact of the liquid sample with the filter pad. Alan J. Gordon (U.S. Pat. No. 4,391,710) accomplished this for Shandon by providing a tilting chamber. John Wells (U.S. Pat. No. 4,428,323) on the other hand provided a well for the sample liquid as a dam against premature release of such sample, as N. G. Anderson had done for the so-called "Fast Analyzer". The force required, and hence the speed of delivery, is determined by the depth of the well and the slope of the dam.

With the above provisions, transitional cell loss is significantly reduced but it still occurs to an undesirable extent. Even with the system of John Wells, the liquid is forced over the dam upon start up and into the flow passage leading therefrom. Cell-carrying sample liquid rushes into the empty flow passage on start up. Since the cells are uniformly suspended in the sample liquid, the initial contact with the filter pad will cause absorption of cell-containing liquid.

Another source of cell loss is during wet fixation after the cells have been collected on the slide. Normally, the collected cells are sprayed with, or the slide is immersed in, an aqueous alcohol fixative solution. Residual liquid on the slide interacts with the fixative solution and, together with the forces involved in applying the solution, often results in dislodging of otherwise adherent cells from the slide.

Some manufacturers recommend addition of fixative liquid into the sample chamber after addition of the cell-containing liquid sample so that cells will be fixed during centrifuging. However, there is no provision for separating the fixative from the sample, and cells become fixed prior to collection on the slide. This results in cells which do not properly flatten and therefore do not adhere well to the slide, thus producing poor morphology and cell loss. No equipment presently exists which provides for in-situ fixation during centrifuging following cell sedimentation.

SUMMARY OF THE INVENTION

The present invention further improves cytocentrifugation apparatus and methods in order to achieve maximum capture of cells by the microscope slide toward which the cell-carrying liquid is passed from the corresponding sample chamber under the impetus of centrifugal force while taking up in a satisfactory manner the liquid component of the liquid sample following cell deposition on the slide.

This has been accomplished by providing an improved device for use with a cytocentrifuge, such device usually having a plurality of liquid-receiving chambers serially related and communicating with and along a conduit in common that leads to a holder for a microscopic slide, which holder is provided by clamping means carried by the rotor and desirably secured thereto. Across the discharge end of the conduit, so as to be within such slide holder, is interposed means for receiving and holding, in fluid-sealing relationship with the confronting face of a slide held by the slide holder, a liquid-absorbent filter pad. As shown, there are at least two of the liquid-receiving chambers arranged serially along the conduit, the devices themselves being arranged in usual multiple fashion in the rotor of a cytocentrifugation machine.

The chambers can be of any type arranged for sequential discharge of their contained liquid into the conduit under centrifuging conditions so long as there are at least two of them. Preferably the chamber located closest in line to the filter pad holder and to the microscope slide holder in each device is positioned above the conduit, with its bottom open and opening into the conduit. A filter pad prewetting solution is preferably placed in such chamber for wetting the filter pad in advance of the passing therethrough of the cell-carrying liquid sample and for providing a liquid barrier between the cell-carrying sample liquid and the filter pad. The sample liquid is preferably placed in the second chamber in line that extends below the conduit as a well for damming against outflow of liquid into the conduit except by the exercise of centrifugal force on such liquid.

It can be seen that, if a filter-pad-prewetting liquid is placed in the chamber that is located closest to the filter pad holder and the slide holder of the cytocentrifuging device, it will precondition the filter pad by prewetting it prior to contact therewith of the cell-carrying liquid sample. When the cell-carrying liquid sample reaches the filter, such filter will have already absorbed advance-flowing liquid that is devoid of cells, and will further restrict lateral flow of the cell-carrying liquid that follows.

Since the cell-carrying liquid sample discharges into and flows through the conduit before the prewetting liquid is completely absorbed, the residual prewetting liquid forms a barrier which prevents the cell-carrying liquid from contacting the filter pad until the final steady-state rotor speed is achieved. At such final rotor speed, maximum sedimentation velocity of the cells will have been achieved, thus minimizing lateral diversion of cells into the filter pad.

Filter pad fabrication may be such, in accordance with the invention, that it is still capable of absorbing the liquid component of the liquid sample even if thinner than usual around the opening through which the sample liquid flows, following extraction of cells therefrom by deposition on and retention by the surface of the slide. To this end, a novel, dual-thickness filter pad is employed which is relatively thin marginally of the liquid flow opening and is otherwise relatively thick, this being achieved either by compressing a single thickness sheet of filter pad material marginally of the opening therethrough or fabricating the filter pad from two sheets of filter pad material with only the desired thicker portion of the final filter pad being double thickness. Alternatively, a usual single thickness filter pad can be used with the provision of a filter-pad-indenting ring as the clamping face of the filter pad clamp, so that the flow rate of the liquid component of the cell-carrying liquid sample into the filter pad will be restricted. Such an indenting ring can be employed advantageously with any type of filter pad.

Further structural features of the invention that contribute to convenience of use of the cytocentrifugation are:

1. The provision of each device with a filter pad holder that is integrally molded with the body of the device from a plastic material for either removal and replacement of a used filter pad when the device is to be reused, or with filter pad molded or tightly held therein for discard with the entire device following use, this being accompanied by means permitting slide removal without distributing cells deposited thereon.
2. Provision of a spring-actuated clamping mechanism for the filter pad holder and slide holder, which is easily opened by means of a manually operated lever arm and which may be and preferably is securely, rather than removably, mounted on the rotor for repeated use with replacement cytocentrifugation sample devices. Such clamping means is prevented from contacting and possibly breaking a glass slide in the absence of the cytocentrifugation device, which is normally not installed on the rotor until a glass slide is placed in the portion of the slide holder provided by the clamping means.
3. Provision for automatically aligning the filter pad relative to the conduit through which the cell-carrying sample liquid and other liquid or liquids are passed.

The multi-chambered device of the invention provides not only for prewetting of the filter pad in advance of the cell-carrying sample liquid reaching the filter pad and the microscope slide, but enables the cells to be fixed on the slide as part of a continuing centrifuging operation. Thus, a fixative liquid may be introduced into the chamber of the plurality of chambers that follows the sample chamber, so that there is sequential flow therefrom following flow of the liquid sample.

From a method standpoint, the invention provides a procedure in the use of the apparatus comprising the steps of placing a cell-carrying liquid sample in a chamber of the plurality of chambers and placing either a filter-pad-wetting liquid in the first in line of the series of chambers toward the filter pad and slide holder or a fixative solution in a chamber that follows in line the liquid sample receiving chamber, and then operating the cytocentrifugation apparatus.

THE DRAWINGS

The best mode presently contemplated for carrying out the invention in actual practice is illustrated in the accompanying drawings, in which:

FIG. 1 represents a view in top plan of a cytocentrifuging rotor of the invention with desirably non-removable clamping means at multiple locations (shown in full lines at two locations and in broken lines at the remaining locations) at which such rotor is adapted to receive respective cytocentrifugation devices (also shown in full lines at the two locations and indicated by broken lines at the remaining locations).

FIG. 2, a fragmentary vertical section taken on the line 2—2 of FIG. 1 and drawn to a somewhat larger scale showing the cytocentrifugation rotor of FIG. 1 as mounted for use on a general purpose centrifugation machine;

FIG. 3, an enlarged, right-hand, fragmentary portion of FIG. 2, showing only the cytocentrifugation device and the clamping assembly means as secured on the rotor;

FIG. 4, a view corresponding to that of FIG. 3, but of an embodiment having a third chamber similar to the second chamber of FIG. 2 and arranged in series with the two chambers of FIG. 2;

FIG. 5, a detail view in perspective drawn to the scale of FIGS. 3 and 4, and looking toward the front of and showing a filter pad placed in filter pad holding means provided as a part of the device of FIGS. 3 and 4 and constructed to receive and shown as holding a replaceable filter pad of conventional type;

FIG. 6, a vertical section taken on the line 6—6 of FIG. 5 and drawn to a larger scale;

FIG. 7, a view corresponding to that of FIG. 5 but showing a completely disposable filter pad receptacle and filter pad, the filter pad having a thin portion marginal to the center opening and being thick otherwise in accordance with one aspect of the invention; and FIG. 8, a vertical section taken on the line 8—8 of FIG. 7 and drawn to the larger scale of FIG. 6.

DETAILED DESCRIPTION OF THE ILLUSTRATED EMBODIMENTS

In the form illustrated in FIGS. 1-4, as well as FIGS. 5 and 6, cytocentrifugation devices 10 of the invention are received by and mounted side-by-side in a cytocentrifugation rotor 11. Each of the devices 10 are multi-chambered in the sense that there are a plurality, in this instance two, liquid-receiving chambers arranged in line successively to discharge sequentially into a conduit in common that leads to holding means for a filter pad 12 FIGS. 5 and 6, or 27, FIGS. 7 and 8, and to holding means for a microscope slide 13, FIGS. 3 and 4.

Figure 2:
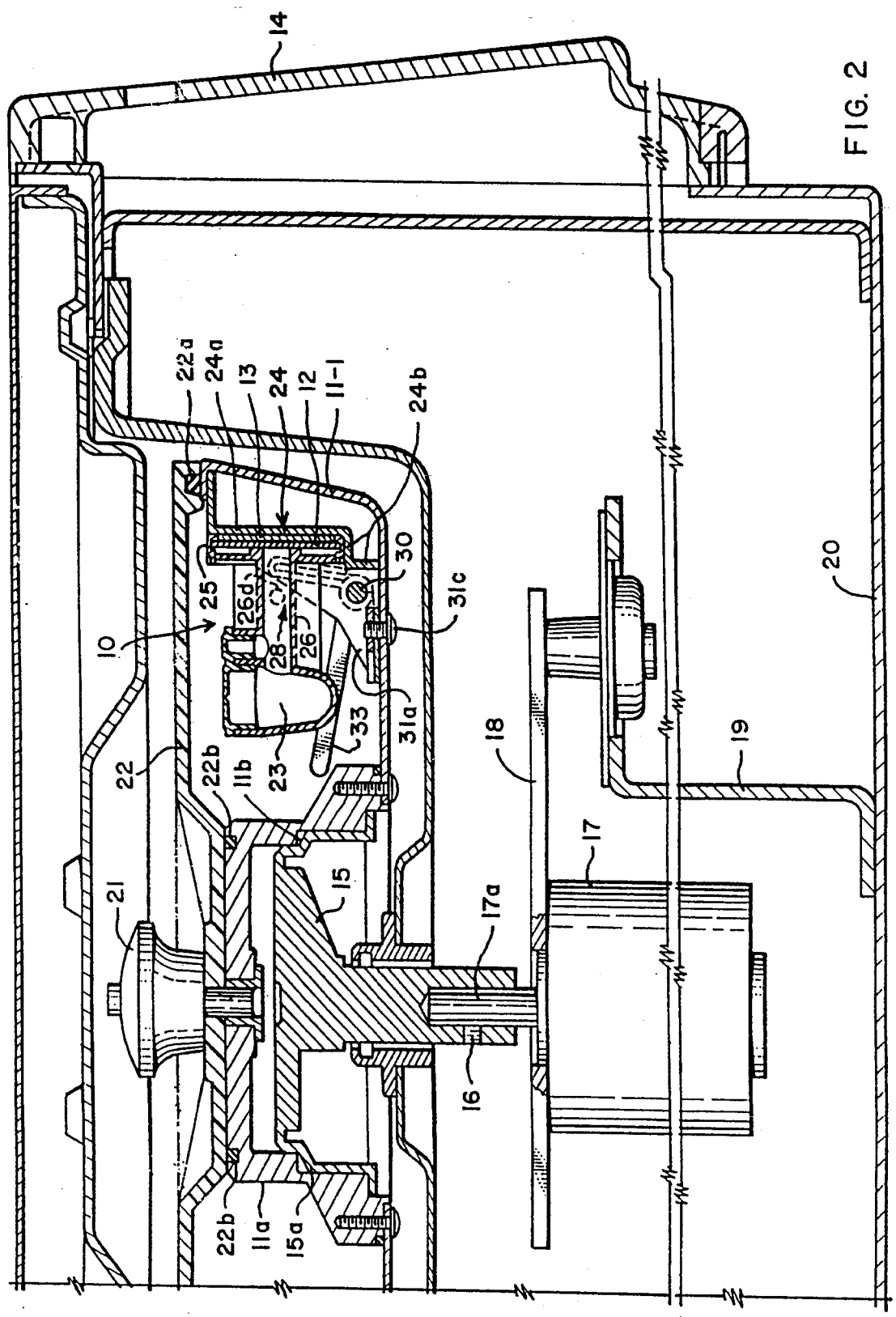

Rotor 11 comprises rotary means preferably, as shown, in the form of a bowl 11-1 that is removably and replaceably mounted for rotation on a general purpose centrifugation machine 14, FIG. 2, which, in this instance, is provided with a hub 15 secured by a set-screw 16 to the drive shaft 17a of an electric motor 17 that is mounted by a bracket 18 on a standard 19 of a housing 20. Hub 15 is received by a recessed fitting 11a opening into the underside of rotor 11 and provided with a circumferential series of grooves 11b for receiving a corresponding series of ribs 15a projecting from hub 15. A grasping knob 21 projects upwardly from a cover 22 for rotor 11 to enable convenient removal and replacement of such rotor on centrifugation machine 14. O-rings 22a and 22b are interposed between cover 22 and rotor 11 to seal against release of biohazardous materials.

The body of each of the cytocentrifugation devices 10, see FIG. 3, is preferably molded integrally from a suitable rigid plastic material, such as a high density polypropylene, to provide a chamber 23 that is open at its top for the reception of a sample of a cell-carrying liquid from which as many of the cells as possible are to be deposited on and retained by the confronting forward face of the microscope slide 13.

Slide 13 is removably inserted in microscope slide holding means, here shown in the form of a slide holder 24 which is preferably provided as part of clamping means and which is juxtaposed relative to a filter pad holder, here shown as a rectangular receptacle 25, into which filter pad 12 is removably inserted through either a top opening 25a thereof. FIGS. 6 and 7, or a side opening as in FIG. 7.

Sample chamber 23 has depth, relative to a conduit 26 connecting it by way of a lateral outlet port 23a in a wall of such chamber with filter pad holder 25, which depth serves as a dam against outflow of the sample liquid contained by such chamber except under the influence of centrifugal force. The speed of discharge of liquid from chamber 23 is determined by the degree of slope of the forward wall 23b of such chamber. It should be noted that a damming arrangement for a chamber holding a liquid to be released only by the exercise of centrifugal force is shown by the aforementioned Wells U.S. Pat. No. 4,428,328 of Jan. 31, 1984, while inclining the damming wall 22b outwardly of the interior of the well to govern speed of liquid discharge is shown by the aforementioned N. G. Anderson "Fast Analyzer" prior art.

Conduit 26 leads from outlet port 23a of chamber 23 to the central area of filter pad holder 25. The filter pad, see 12, may be removable from and replaceable in its holder 25, as in FIGS. 1 through 6, or the filter pad may be molded or tightly inserted in an alternative form of filter pad holder as is the dual thickness filter pad 27 shown in FIGS. 7 and 8. In either event, the filter pad is provided with preferably a central opening 12a, or 27a through which the liquid from the sample chamber must pass to reach the confronting face of boss 26b of the slide.

The relative magnitudes of cell sedimentation velocity and lateral liquid flow will determine whether a significant number of the cells in the sample liquid from the sample chamber will be lost to the slide by passing laterally into the filter pad before contacting, or even after contacting but failing to stick to, the confronting face of the microscope slide. To minimize loss of cells into the filter pad, the speed of sedimentation of cells onto the slide should exceed the lateral speed of travel of the liquid component into the filter pad.

To accomplish this, it is preferred that the filter pad be relatively thin marginally of the opening therethrough for liquid extracting purposes and relatively thick beyond that for liquid storing purposes. However, conventional single thickness filter pads can be used and, in both instances, a sharp circular ridge 26a, FIG. 4 may be provided, either as or on the clamping face of the clamping boss 26b, which is formed by the liquid discharge end of conduit 26 that protrudes immediately beyond the clamping plate member 26c, or such clamping face may be left flat as in FIG. 3.

Figure 1:
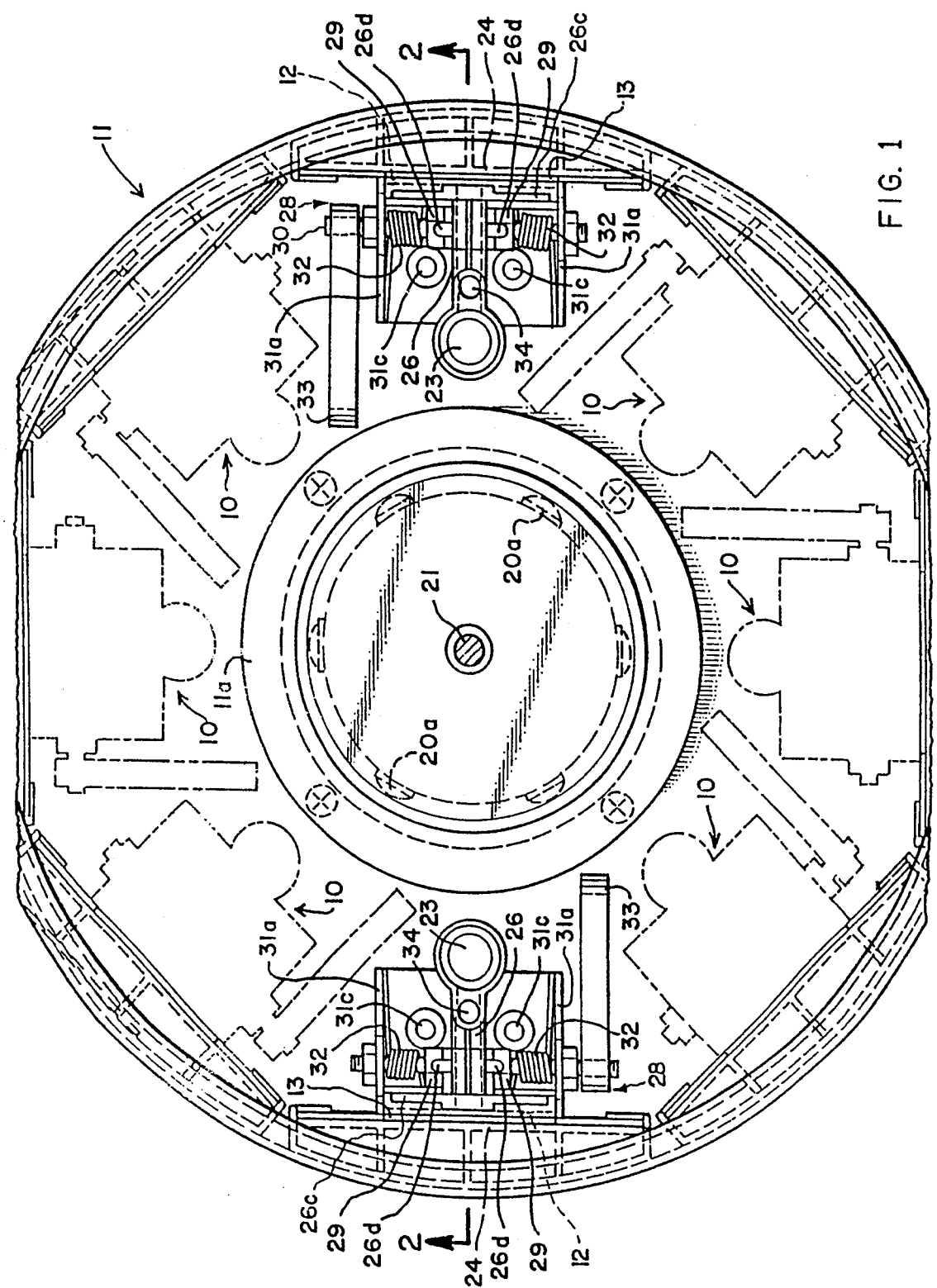

The clamping means is indicated at 28 as an assembly including holder 24. It is secured to the rotary mean, here bowl 11-1, of rotor 11 so as to remain in place when the corresponding microscope slide 13, filter pad 12, and cytocentrifugation device 10 are removed from he rotary means of the rotor after a given run of the cytocentrifugation apparatus in which they are installed. Thus, holder 24 is preferably made as shown in FIGS. 1 and 4. As shown FIGS. 1, 3, and 4. Wall means, comprising a first set of walls, i.e. an upper wall member 24a and a lower wall member 24b formed as a step, both upstanding relative to the normally horizontal placement of the rotor and fixedly attached to bowl 11-1, define such holder 24. Such wall member 24a and step member 24b extend transversely of the longitudinally extending conduit 26 of a received cytocentrifugation device 10. A pair of clamping arms 29 are fixed on a shaft 30 that is rotatably inserted in and between a separate second set of walls 31a, respectively, of the aforesaid wall means upstanding laterally from a base plate 31 that is fixedly secured to rotor 11, as by screws 31c, FIGS. 3 and 4, which preferably have seals such as O-rings (not shown) interposed between the rotor and the screw heads for confining biologically hazardous materials within the closed rotor. At such transverse wall member 24a, such arms 29 are normally held in clamping position against a first abutment means defined by a filter pad clamping plate member 26c extending transversely from conduit 26 immediately behind the protruding, liquid discharge end of such conduit. A pair of coil springs 32, respectively, see especially FIG. 1, on opposite end portions of shaft 30 have respective ends 32a that bear against e.g. connect with, such clamping arms 29 and force them toward and against clamping plate 26c. For relieving clamping pressure, shaft 30 is provided with a handle 33 which is fixedly secured to one end thereof and extends substantially perpendicularly therefrom for manipulation by the user when it is desired to remove the slide, the filter pad, and the cytocentrifugation device 10 from the rotor 11. In instances in which the filter pad is secured in its holding receptacle 25, as by molding the receptacle therearound as in FIGS. 7 and 8, or is inserted in and tightly held by holding receptacle 25 against removal therefrom, the entire receptacle will be removed from base plate holder 31 rotor 11 and discarded following deposition of the cells on the slide which is separately removed. Clamping assembly 28 will remain attached to rotor 11 for reuse.

Respective recesses 25b are provided in filter-pad-holding members 25c that extend along the top and bottom of filter-pad-holding receptacle 25 to prevent scraping of cells that have been deposited on a slide 13 during centrifugation when the device 10 is removed from rotor 11 following centrifugation.

A second abutment means defined by a pair of pins 26d, respectively, are provided on and extend transversely from conduit 26 in back of the clamping arms 29 to retract the device 10 from clamped position when lever 33 is depressed and arms 29 are pivoted backwardly against such pins 26d at such time as a centrifugation operation is completed.

The second chamber 34 is positioned above conduit 26 and has its bottom open and opening thereinto, as at 34a. It is located closer to the filter pad holder than is sample chamber 23. The open tops of both the chambers 23 and 34 are normally tightly closed, after being filled with their respective liquids, by an elongate insertable cap 35.

A filter pad wetting liquid, e.g. saline solution, is placed into chamber 34 which is sized to receive only a few droplets of the wetting liquid, typically two-hundred microliters, so surface tension will prevent movement backward or forwardly in conduit 26 of such wetting liquid except under centrifugal force when such liquid will flow toward and into the opening 12a or 27a of the filter pad in advance of the liquid sample from chamber 23.

It should be noted that, contrary to instances in which prewetting liquid has been applied to filter pads of prior art cytocentrifugations, there is here application of the prewetting liquid as part of a continuing run of the centrifugation both for prewetting the filter and for forming a barrier between the cell-carrying sample liquid and the filter pad.

When a third chamber 36, FIG. 4, similar to chamber 23, is provided in series with chambers 23 and 34, the forward chamber 34 will be used for prewetting solution, while chamber 23 will be used for the sample liquid and the final chamber 36 will be used for a fixative solution, such as fifty percent aqueous alcohol, for fixing the cells onto the slide.

The filter pad 27 of FIGS. 7 and 8 is conveniently made by compressing the marginal area of a thicker than usual filter pad sheet material to form a relatively thin and dense portion 27b circumferentially of the central opening 27a and a relatively thick and porous portion 27c for the remainder of the filter pad, but can be made by placing two sheets together.

It should be noted that the set of clamping arms 29 are pivotally mounted by shaft 30 for back and forth movement along the longitudinal axis of the corresponding cytocentrifugation device 10 back of the liquid discharge end portion thereof for exerting resiliently activated clamping pressure against the laterally extending clamping plate member 26c thereof at respective opposite sides of conduit 26 of such cytocentrifugation device 10, and that such device 10 is retracted against the resiliently activated clamping pressure of the clamping arms 29 by manually pushing down on handle lever 33, whereby clamping pressure on the slide 13, the filter pad 12, and the cytocentrifugation device 10 is released and these items can be removed from rotor 11 for replacement, desirably leaving the clamping assembly 28 as secured in place in bowl 11-1 of the rotor.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. For use with cytocentrifugation apparatus, an improved cytocentrifuge rotor of the type having rotary means adapted for installation in said cytocentrifugation apparatus and for removably receiving and holding a plurality of cytocentrifugation devices that are adapted to carry, during centrifugation, a cell-containing liquid for delivery through a discharge end of said device to a juxtaposed filter pad and microscope slide, said improved cytocentrifuge rotor comprising in combination a clamping assembly for each said cytocentrifugation device that may be held by said rotary means and for a therewith associated filter pad and microscope slide, each said clamping assembly comprising wall means defining an elongate holder adapted for receiving and removably holding in juxtaposed positions during use of said rotor, a microscope slide, a filter pad, and the discharge end portion of the corresponding cytocentrifugation device, a set of clamping arms pivotally mounted by said wall means on an axis that is horizontal during use of said apparatus for back and forth movement along said corresponding cytocentrifugation device in advance of said holder, resilient means normally urging said clamping arms toward said holder, and means associated with said pivotally mounted clamping arms for moving said clamping arms away from said holder against the clamping urge of said resilient means and to release said corresponding cytocentrifugation device, filter pad, and slide for removal from the corresponding clamping assembly and from the rotary means; said set of clamping arms being fixedly mounted on a pivot shaft that is rotatably mounted in said wall means of said clamping assembly and that extends horizontally during cytocentrifugation for confronting the holder of such clamping assembly, and the means for moving the clamping arms away from said holder being a handle in the form of a manually manipulatable lever arm fixedly secured to and operatively extending substantially perpendicularly from said shaft for rotating said shaft against the urging of said arms by said resilient means.

2. A cytocentrifugation rotor according to claim 1, wherein the wall means includes a first set of walls defining the holder and a separate second set of walls in which the arms are pivotally mounted.

3. A cytocentrifugation rotor according to claim 1, wherein means are provided securing each said clamping assembly to said rotary means against removal when the corresponding cytocentrifugation device and associate filter pad and microscope slide are removed.

4. The improved cytocentrifugation rotor of claim 1 wherein the lever arm extends from an end of said shaft.

5. A cytocentrifugation rotor, comprising: a plurality of cytocentrifugation devices rotary means adapted for installation in cytocentrifugation apparatus and to removably receive and hold said plurality of cytocentrifugation devices that are each adapted to carry, during centrifugation, a cell-containing liquid for delivery through a discharge end of said device to juxtaposed filter pad and microscope slide; a clamping assembly for each said cytocentrifugation device that may be held by said rotary means and for a therewith associated filter pad and microscope slide, each said clamping assembly comprising wall means defining a holder for receiving and removably holding a microscope slide, a filter pad, and the discharge end portion of the corresponding cytocentrifugation device in juxtaposed positions, a set of clamping arms fixedly mounted on a shaft that is pivotally mounted in said wall means so that said arms execute back and forth movement along said corresponding cytocentrifugation device in advance of said holder, resilient means normally urging said clamping arms toward said holder and against a first abutment means of the corresponding cytocentrifugation device to clamp the device and corresponding filter pad and microscope slide against said holder, and means associated with said pivotally mounted clamping arms for moving said clamping arms in a path of releasing movement away from said holding means against the clamping urge of said resilient means and to release said corresponding cytocentrifugation, filter pad, and slide for removal from the corresponding clamping assembly and the rotary means; each said cytocentrifugation device having second abutment means extending into said path of releasing movement of said clamping arms for pushing by said clamping arms to move said cytocentrifugation device away from the corresponding holder, whereby said moving of the clamping arms backwardly will cause them to engage said second abutment means of said cytocentrifugation device and push said device backwardly against the clamping force of said resilient means to release said microscope slide, said filter pad, and said cytocentrifugation device so they can be removed from said clamping assembly and from said rotary means.

6. A cytocentrifugation rotor according to claim 5, wherein the wall means includes a first set of walls defining the holder and a separate second set of walls in which the arms are pivotally mounted.

7. A cytocentrifugation rotor according to claim 5, wherein means are provided securing each said clamping assembly to said rotary means against removal when the corresponding cytocentrifugation device and associated filter pad and microscope slide are removed.

8. A cytocentrifugation rotor according to claim 5, wherein the means for moving the clamping arms away from said holder is a manually manipulatable handle in the form of a lever arm fixedly secured to and operatively extending substantially perpendicularly from said shaft for rotating said shaft against the urging of said arms by said resilient means.

9. The improved cytocentrifugation rotor of claim 8 wherein the lever arm extends from an end of said shaft.

10. A cytocentrifugation rotor according to claim 5, wherein the second abutment means are pins secured to and extending from opposite sides of the cytocentrifugation device into the respective paths of releasing movement of said clamping arms.

* * * * *